US00PP15086P2

(12) United States Plant Patent
Westhoff

(10) Patent No.: US PP15,086 P2
(45) Date of Patent: Aug. 17, 2004

(54) SCAEVOLA PLANT NAMED 'WESSCAEAQUA'

(50) Latin Name: *Scaevola aemula*
Varietal Denomination: Wesscaeaqua

(75) Inventor: Heinrich Westhoff, Südlohn (DE)

(73) Assignee: Joseph & Heinrich Westhoff Gartenbrau-Spezialkulturen, Südlohn-Oeding (DE)

( * ) Notice: Subject to any disclaimer, the term of this patent is extended or adjusted under 35 U.S.C. 154(b) by 0 days.

(21) Appl. No.: 10/602,103

(22) Filed: Jun. 23, 2003

(51) Int. Cl.[7] ..... A01H 5/00
(52) U.S. Cl. ..... Plt./363
(58) Field of Search ..... Plt./363

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Scaevola plant named Wesscaeaqua, characterized by its cascading and uniformly rounded plant habit; freely branching plant habit; vigorous growth habit; and numerous violet blue-colored fan-shaped flowers with white-colored centers.

1 Drawing Sheet

Botanical classification/cultivar designation: *Scaevola aemula* cultivar Wesscaeaqua.

BACKGROUND OF THE INVENTION

The present Invention relates to a new and distinct cultivar of Scaevola plant, botanically known as *Scaevola aemula* and hereinafter referred to by the cultivar name 'Wesscaeaqua'.

The new cultivar is a product of a planned breeding program conducted by the Inventor in Sudlohn-Oeding, Germany. The new Scaevola originated from a cross-pollination of the Scaevola cultivar Fancy, disclosed in U.S. Plant Pat. No. 9,867, as the female, or seed, parent with a proprietary selection of *Scaevola aemula* identified as code number 110, not patented, as the male, or pollen, parent. The new Scaevola was selected by the Inventor in 2001 as a single plant within the progeny of the cross-pollination in a controlled environment in Sudlohn-Oeding, Germany.

Asexual reproduction of the new cultivar by terminal cuttings taken at Sudlohn-Oeding, Germany since 2001, has shown that the unique features of this new Scaevola are stable and reproduced true to type in successive generations.

SUMMARY OF THE INVENTION

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be the basic characteristics of 'Wesscaeaqua', which distinguish 'Wesscaeaqua' as a new and distinct cultivar:

1. Cascading and uniformly rounded plant habit.
2. Freely branching habit, dense and bushy plant form.
3. Vigorous growth habit.
4. Numerous violet blue-colored flowers with white-colored centers.

Plants of the new Scaevola can be compared to plants of the female parent, the cultivar Fancy. In side-by-side comparisons conducted by the Inventor in Sudlohn-Oeding, Germany, plants of the new Scaevola and the cultivar Fancy differed in the following characteristics:

1. Plants of the new Scaevola had longer internodes than plants of the cultivar Fancy.
2. Leaves of plants of the new Scaevola were shorter and more ovate in shape than leaves of plants of the cultivar Fancy.
3. Flowers of plants of the new Scaevola were lighter violet blue in color and had larger white-colored centers than flowers of plants of the cultivar Fancy.

Plants of the new Scaevola can be compared to plants of the male parent, the proprietary selection identified as code number 110. In side-by-side comparisons conducted by the Inventor in Sudlohn-Oeding, Germany, plants of the new Scaevola and the male parent selection differed in the following characteristics:

1. Plants of the new Scaevola were more freely branching than plants of the male parent selection.
2. Leaves of plants of the new Scaevola were longer and darker green in color than leaves of plants of the male parent selection.
3. Plants of the new Scaevola were more freely flowering than plants of the male parent selection.
4. Plants of the new Scaevola had larger flowers than plants of the male parent selection.

Plants of the new Scaevola can also be compared to plants of the cultivar Brilliant, disclosed in U.S. Plant Pat. No. 12,099. In side-by-side comparisons conducted by the Inventor in Sudlohn-Oeding, Germany, plants of the new Scaevola and the cultivar Brilliant differed in the following characteristics:

1. Plants of the new Scaevola had longer internodes than plants of the cultivar Brilliant.
2. Plants of the new Scaevola had fewer flowers per inflorescence than plants of the cultivar Brilliant.
3. Flowers of plants of the new Scaevola were lighter violet blue in color than flowers of plants of the cultivar Brilliant.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Scaevola.

The photograph at the top of the sheet is a close-up view of a typical inflorescence of 'Wesscaeaqua'.

The photograph at the bottom of the sheet comprises a side perspective view of a typical plant of 'Wesscaeaqua' grown in a container.

DETAILED BOTANICAL DESCRIPTION

Plants used in the aforementioned photographs and for the following description were grown under conditions which closely approximate commercial production conditions during the spring and summer in a glass-covered greenhouse in Sudlohn-Oeding, Germany. Plants were about 20 weeks from planting rooted cuttings in 12-cm containers. During the production of the plants, the day temperatures ranged from 20 to 25° C., night temperatures ranged from 16 to 18° C., and light levels ranged from 3,000 to 50,000 lux. Plants were pinched about three to four weeks after planting and then given a second pinch about four weeks later.

In the following description, color references are made to The Royal Horticultural Society Colour Chart, 2001 Edition, except where general terms of ordinary dictionary significance are used.

Botanical classification: *Scaevola aemula* cultivar Wesscaeaqua.

Parentage:

*Female, or seed, parent.*—*Scaevola aemula* cultivar Fancy, disclosed in U.S. Plant Pat. No. 9,867.

*Male, or pollen, parent.*—Proprietary selection of *Scaevola aemula* identified as code number 110, not patented.

Propagation:

*Type cutting.*—Terminal cuttings.

*Time to develop roots.*—About four weeks at 22° C.

*Rooting habit.*—Fine, fibrous, and freely branching.

Plant description:

*Plant form and growth habit.*—Annual container and garden plant. Cascading and uniformly mounded plant habit; eventually plants become roughly spherical in shape. Suitable for hanging basket, window box and patio containers. Freely branching with lateral branches potentially forming at every vegetative leaf axil when pinched; dense and bushy plant form. Vigorous growth habit.

*Plant height* (*soil level to top of plant plane*).—About 17 to 24 cm.

*Plant length* (*soil level to apices of lateral branches*).—About 66 to 99 cm.

*Stem description.*—Lateral branch length: About 45 to 68 cm. Lateral branch diameter: About 2.3 mm. Main branch length: About 60 to 90 cm. Main branch diameter: About 4 mm. Internode length: About 5.5 cm. Texture: Sparsely pubescent. Color: 144A slightly overlain with 166A.

*Foliage description.*—Arrangement: Alternate, simple; sessile. Length: About 3.5 to 5.5 cm. Width: About 1.8 to 2.6 cm. Shape: Ovate to elliptic. Apex: Acute. Base: Attenuate. Margin: Irregularly serrated, slightly serrated towards base and more strongly serrated towards apex. Texture, upper and lower surfaces: Pubescent, rough and somewhat leathery. Color: Developing leaves, upper surface: 137A to 137B. Developing leaves, lower surface: 146B. Fully expanded leaves, upper surface: 147A. Fully expanded leaves, lower surface: 147B. Venation, upper surface: 147A. Venation, lower surface: 144A.

Flower description:

*Flower type and shape.*—Zygomorphic, semi-circular, fan-shaped flowers with five petals fused at the base to form a tubular flower throat. Flower throat open along the upper surface exposing reproductive organs. Flowers persistent. No fragrance detected.

*Flower arrangement and quantity.*—Solitary flowers arise from leaf axils with one flower per axil. Flowers held outwardly on upturned lateral apices. Freely flowering, typically about five to six open flowers per inflorescence.

*Flowering time.*—Plants flower continuously from May until frost. Flowers typically last at least four days on the plant.

*Flower buds.*—Shape: Lanceolate. Length: About 5 to 18 mm. Diameter: About 2.4 mm. Color: 146C to 146D becoming closer to 145A with development.

*Perianth.*—Aspect: Fan-shaped, flat. Length, fan: About 3 to 3.8 cm. Width, fan: About 1.65 cm.

*Petals.*—Quantity: Five, fused at base. Shape: Oblanceolate to ovate. Apex: Cuspidate. Margin: Entire. Length, above tube: About 1.5 cm. Width, above tube: About 6 mm. Length, tube: About 1.25 cm. Diameter, tube opening: About 4 mm. Diameter, tube: About 2 mm. Texture, upper and lower surfaces: Smooth; flower throat, whiskered. Color: When opening, upper surface: 90B to 90C. When opening, lower surface and tube: 90D; mid-section, 145A to 145B. Fully opened, upper surface: 90C to 90D; towards the base, 155D; at fused base, 9A; venation, 90D; color becoming closer to 90B to 90C with development. Fully opened, lower surface and tube: 90D, mid-section, 145D; venation, 145A to 145D. Throat: 153B, venation, N77A. Tube: 160B; venation, N77A.

*Sepals.*—Quantity and arrangement: One large sepal, two smaller sepals lateral to larger sepal. Length: Larger sepal, about 1.3 cm; lateral sepals, about 7 mm. Width: Larger sepal, about 6 mm; lateral sepals, about 1 mm. Shape: Larger sepal, spatulate; lateral sepals, acicular, needle-like. Apex: Acute. Margin: Larger sepal, serrated; lateral sepals, entire. Texture, upper and lower surfaces: Leathery, slightly pubescent. Color, upper surface: 147A. Color, lower surface: 147B.

*Reproductive organs.*—Androecium: Stamen quantity per flower: About five. Anthers: Shape: Oval. Length: About 2 mm. Diameter: About 1 mm. Color: 11B. Pollen: Sparse. Pollen color: 166B. Gynoecium: Pistil quantity per flower: One. Pistil length: About 1.4 cm. Style length: About 8 mm. Style color: 144D overlain with N79A. Stigma shape: Elongate. Stigma color: Apex, 155D; mid-section and base, 144D. Ovary color: 144A.

*Seed/fruit.*—Seed and fruit production has not been observed.

Disease/pest resistance: Plants of the new Scaevola have been noted to be resistant to pathogens and pests common to Scaevola.

Temperature tolerance: Plants of the new Scaevola have been observed to be tolerant to temperatures ranging from 2 to 30° C.

It is claimed:

1. A new and distinct Scaevola plant named Wesscaeaqua, as illustrated and described.

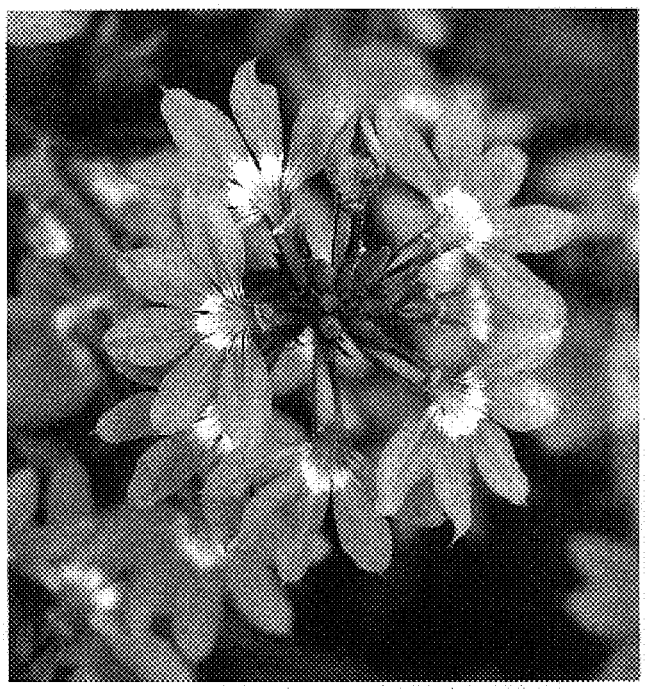
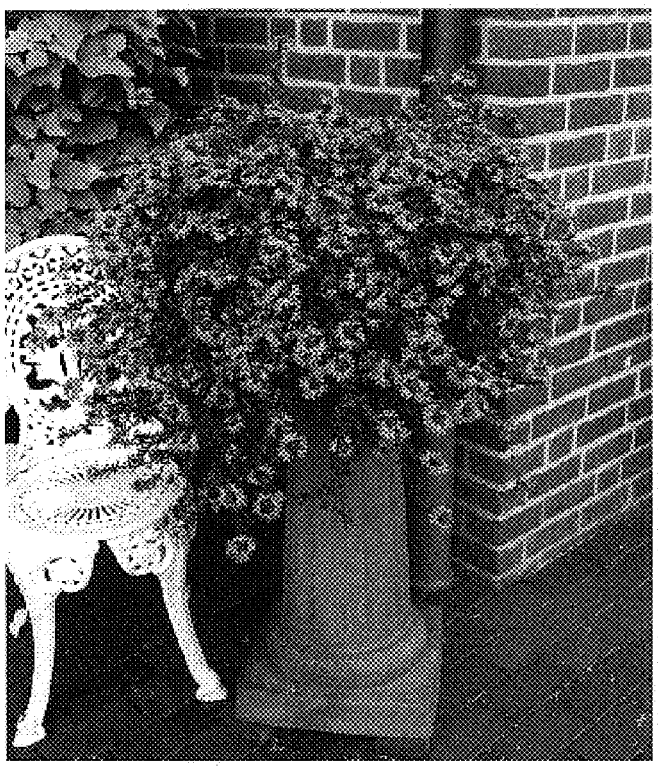

* * * * *